Figure 1:
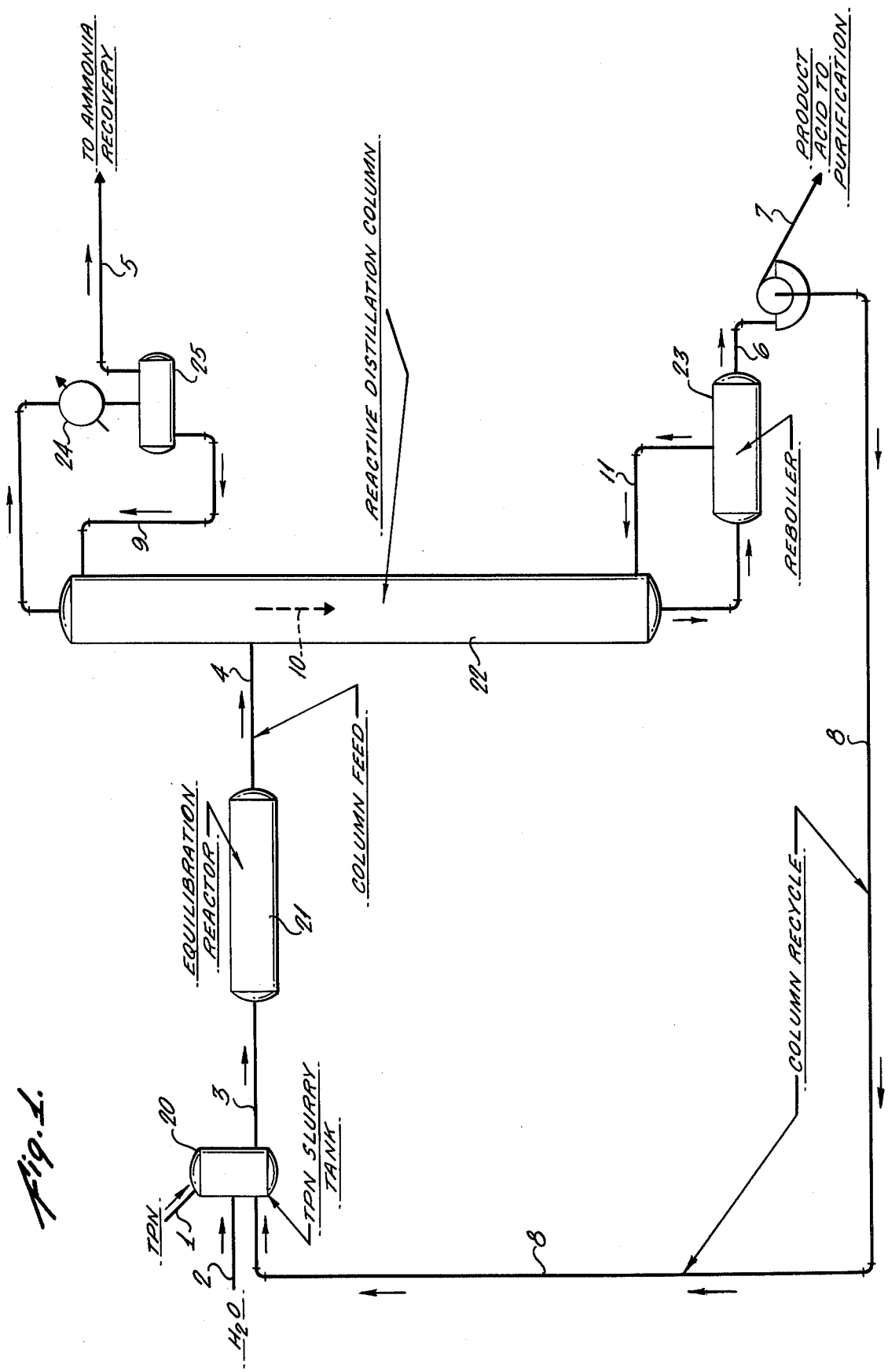

United States Patent [19]

Wynkoop et al.

[11] 4,086,270

[45] Apr. 25, 1978

[54] PROCESS FOR MAKING TEREPHTHALIC ACID

[75] Inventors: Raymond Wynkoop; Allen W. Hancock, II, both of Media, Pa.

[73] Assignee: Suntech, Inc., Wayne, Pa.

[21] Appl. No.: 733,617

[22] Filed: Oct. 18, 1976

[51] Int. Cl.$^2$ .................... C07C 51/08; C07C 63/26
[52] U.S. Cl. .............................................. 260/515 P
[58] Field of Search .................................. 260/515 P

[56] References Cited

U.S. PATENT DOCUMENTS

| 3,873,610 | 3/1975 | Norton | 260/515 P |
|---|---|---|---|
| 4,034,005 | 7/1977 | Hancock et al. | 260/515 P |

Primary Examiner—Jane S. Myers
Attorney, Agent, or Firm—J. Edward Hess; Donald R. Johnson; Paul Lipsitz

[57] ABSTRACT

A process for making terephthalic acid of high purity by feeding an aqueous equilibrium hydrolysis solution of terephthalonitrile to a reactive distillation column operated at a temperature of from about 200° C to about 260° C at autogenous pressure where the equilibrium solution is subjected simultaneously to further hydrolysis and distillation of ammonia while maintaining the concentration of aromatic materials in the aqueous liquid in said column sufficiently high to effect precipitation of dissolved terephthalic acid, removing the water vapor and ammonia from the top of the column, subjecting bottoms product in said column to further hydrolysis and distillation in a reboiler, returning vapor from the reboiler to the distillation column, removing an aqueous slurry of terephthalic acid from the reboiler and separating terephthalic acid product.

1 Claim, 2 Drawing Figures

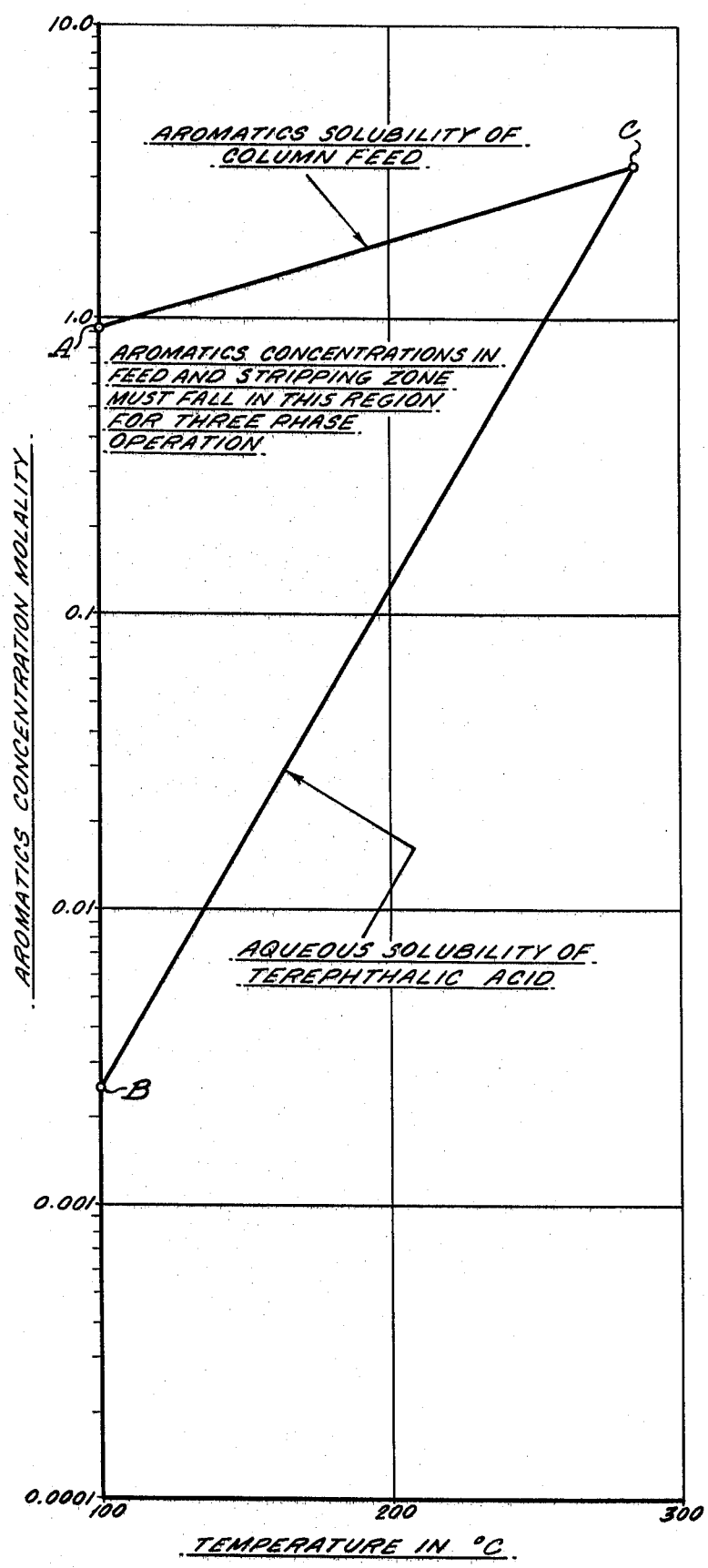

PROCESS FOR MAKING TEREPHTHALIC ACID

It is known in the art to prepare aromatic carboxylic acids by hydrolysis of the corresponding nitriles which in turn, are prepared by ammoxidation of alkyl-substituted hydrocarbons. The acids obtained from such processes must generally have high purity and be essentially devoid of nitrogen containing by-products and, in the case of polycarboxylic acids, must also be free of any by-product monoacids. This is particularly true of aromatic dicarboxylic acids such as terephthalic acid which is the well-known intermediate to polyester fibers. In order to employ terephthalic acid for such use it must have a very high purity and, in particular, be free of nitrogen containing bodies which will discolor the polymer made from such acid, and it must also be free of mono-acids such as p-toluic acid which might arise from incomplete ammoxidation since such a mono-acid would adversely affect polymerization of the acid in that the necessary high molecular weight polymer could not be obtained.

It is known from the disclosure of our application, Ser. No. 565,509, filed Apr. 7, 1975, now abandoned, that hydrolysis of an aromatic nitrile and simultaneous removal of ammonia by-product in a distillation reactor system and subsequent hydrolysis of the bottoms product in a reboiler enables an acid product to be obtained which is of high purity and low in nitrogen by-products. Such process is a two-phase system in which only liquid and vapor are present in the distillation reactor.

An improvement in the process of Ser. No. 565,509 has now been found which enables terephthalic acid to be obtained with still higher purity. In accord with the invention, a process is provided for making terephthalic acid of high purity from the hydrolysate of terephthalonitrile, preferably obtained by ammoxidation of an alkyl aromatic compound, by feeding an equilibrium hydrolysis solution of terephthalonitrile to a reactive distillation column operated at a temperature of from about 200° to about 260° C and at autogenous pressure and maintaining the molal concentration of aromatics in the aqueous liquid in said column sufficiently high to effect precipitation of dissolved terephthalic acid while subjecting the contents of the reactor to further hydrolysis and distillation of ammonia, concentrating ammonia by rectification in the upper portion of the column, removing the concentrated aqueous ammonia vapor from the top of the column, subjecting the remaining equilibrium hydrolysis mixture (i.e., the bottoms product in said column) to further hydrolysis and distillation in a reboiler operated at about 200° to about 260° C, returning vapors from the reboiler to the lower portion of the distillation column, removing an aqueous slurry of product from the reboiler, and separating terephthalic acid product.

The invention as described above involves a reactive distillation in a three phase system (e.g., liquid, solid and gas). The term "reactive distillation" is used herein to indicate the production of free aromatic carboxylic acid by the efficient removal of ammonia from a reaction zone where the normally equilibrium limited reaction of amide and ammonium salt is shifted to the salt which, in turn, yields free acid of high purity. Thus, for example, in the hydrolysis of terephthalonitrile in a closed system the chemistry is as follows:

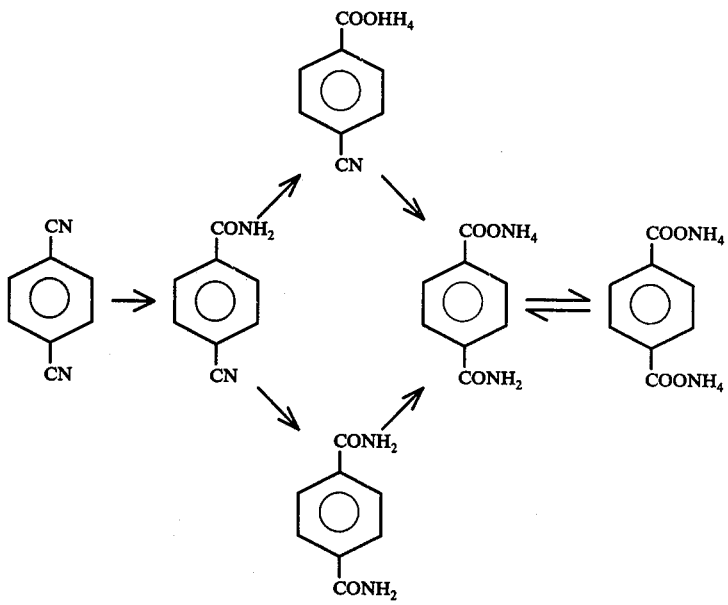

When such a hydrolysis mixture is subjected to reactive distillation the equilibria:

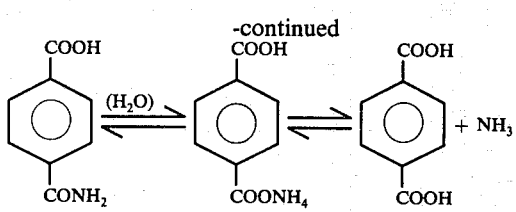

is shifted to favor terephthalic acid in the column because under the temperature conditions within the unit the ammonium salts are converted to the aromatic free acid and ammonia, the ammonia being removed continuously from the reaction zone. Thus, all of the amide nitrogen eventually becomes converted to ammonia and a high purity free acid results as product.

One of the major advantages of the process of this invention is that it enables in a single step:
(a) the concentration of ammonia,
(b) its very efficient removal from the system,
(c) elimination of the undesired nitrogen impurities and
(d) the making of high purity free acid. This is to be contrasted with prior art techniques which sweep ammonia from the system without concentration, thus requiring large volumes of steam. Furthermore, prior art methods yield the ammonium salts as intermediates and require one or more additional steps for conversion to the free acid.

To explain more fully the invention reference is now made to the FIG. 1. The terephthalonitrile (TPN) to be hydrolyzed is fed from a slurry tank 20 through line 3 into a closed hydrolytic chamber 21 where hydrolysis occurs at a temperature between about 200° and about 325° C under autogeneous pressure, the pressure actually rising to about 220 to about 1750 psia. In this reactor, the hydrolysis proceeds until an equilibrium is reached which at the preferred range of about 250° to about 325° C requires from about 2 to about 0.1 hours. The hydrolysis products in the equilibrium mixture as shown above, will consist essentially of the diammonium salt of terephthalic acid and ammonium terephthalamate together with small amounts of the ammonium salt of 4-cyanobenzoic acid, 4-cyanobenzamide, and terephthalamide. After the equilibrium is established the aqueous solution is fed through line 4 into a reactive distillation column 22. It will be understood that a pressure reducing valve in line 4 (not shown) will be used to reduce the pressure of the feed from the pressure in the hydrolyzer to that in the column if the hydrolyzer is operated at a temperature higher (and thus pressure) than that of the column. On the other hand, a pump will be needed in line 4 (not shown) to increase the stream pressure if the hydrolyzer is operated at a lower temperature than that of the column. It is in the column 22 where the removal of ammonia from the salts leads to the production of free acids. Also in this column the further hydrolysis of nitrogen-containing aromatics occurs in the stripping section while concentration of the resulting ammonia occurs in the rectifying section. It is in this way that the equilibrium is shifted by removal of ammonia taken overhead together with water vapor through heat exchanger 24 to condenser 25. The distillate product is recovered in the usual fashion with a portion of the overhead being returned to the column through line 9 as reflux. The reactor column is operated at a temperature between about 200° and about 260° C at autogeneous pressure which will be a pressure of between about 220 and about 685 psia.

The molal concentration of the aromatics in the aqueous liquid phase within said column is maintained at a concentration effective to precipitate terephthalic acid from solution. The term "aromatics" or "aromatic materials" is used to indicate the numerous components of the various equilibria indicated above. As indicated, the process maintains the concentration of these aromatics in the column sufficiently high to cause precipitation of solid terephthalic acid. That is, the aqueous liquid will be saturated with respect to terephthalic acid and solid acid will be present as a third phase of the system. This effective concentration is achieved readily by controlling the amount of water used in the hydrolysis reaction and as can be seen from FIG. 1 may most easily be controlled by the water input line 2 to the slurry tank 20. The system is readily controlled by monitoring the bottoms product concentration from the reboiler and adjusting the feed water flow so that the terephthalic acid solubility limit will be exceeded in the stripping zone of the column thereby causing precipitation of the free terephthalic acid.

It has been found that in the operation of the process at 200° to 260° C, molal solubility concentration of pure TPA will generally be between about 0.1 at about 200° C to about 1.5 at the highest temperature while the molal solubility of the feed material is between about 1.9 molal and about 2.9 molal. Thus, for a given temperature there is an upper and lower temperature range within which the molal concentration of the aromatics must fall for three phase operation to occur. FIG. 2 illustrates in graphic form, this relationship between temperature and aromatics concentration for operating the process in a three phase system. As indicated above, an equilibrated ammonium salt solution obtained from terephthalonitrile hydrolysis enters the column and combines with liquid reflux. Due to their low vapor pressure the aromatic components remain essentially in the stipping section of the column. As the aromatic salts progress down the stipping section they are converted to acids by the removal of ammonia. As more salts are converted the concentration of terephthlic acid increases and exceeds its solubility limit leading to its precipitation. For the system to function as described above, the aromatices concentration in both the feed and stripping zone of the column must fall within the region bounded by lines AC and CB of FIG. 2. If the concentration is above line AC, the feed will be a slurry rather than a solution. On the other hand, when the aromatics concentration is below line BC, then TPA product will all be in solution and no three phase system can exist however high the conversion of the feed ammonium salts to free acid in the column. The solubility boundaries converge at about 280° C and a preferred maximum operating temperature is about 260° C. In general due to the low reaction rates at temperatures below 200° C, a very long uneconomical residence time would be required to achieve desired product purity, so that a temperature of about 200° C becomes a practical minimum. It will be understood that although temperatures below about 200° C are shown in FIG. 2, the actual operation of the process of the invention will be carried out at from about 200° to about 260° C as set out above.

It is important that the residence time of materials within the column be longer than that found in simple distillation systems and a preferred method to accomplish an increased residence time is by means of the apparatus disclosed in the copending application of Allen W. Hancock II, Ser. No. 463,493, filed Apr. 24, 1974, now abandoned, which employs liquid reservoirs between trays within the columns. In the process of this invention, residence time will be preferably between about 30 and about 180 minutes. These long residence times are necessary to provide time to enable the amides in the equilibrium hydrolysis system to be shifted toward the salt as the ammonia is removed as explained above. To separate the ammonia effectively, only moderate reflux ratios on the order to 2 to 10 are required. A particular advantage of this portion of the process is that the actual water carried over is only a small fraction of the water in the feed. Thus, for example, a typical feed concentration to the column reactor may contain one mole of aromatic material to 50 moles of water and, even if the mole percent of water in the overhead is quite high (e.g., 50 mole %), the actual quantity of water carried over is only a small fraction of the feed (about 4%). Likewise, the ammonia content is significantly concentrated. For example, the ammonia concentration of the hydrolysate input is about 4 mole percent, but after concentration by rectification in the columm it exits at no less than about 50 mole percent. Furthermore, there is no carry-over of aromatic compounds in the overhead. It is clear that one major advantage of the process is that the utility requirements are low and, thus, a highly efficient process is achieved. This is in contrast to known techniques where ammonia is removed by steam sweeping which often requires that the quantity of steam be that or approach that of the feed itself and this high steam volume militates against an economical process.

The terephthalic acid product which flows to the bottom of the column will consist of a mixture of dissolved and precipitated solid terephthalic acid. This mixture is taken to a reboiler 23 where any residual intermediate materials are further converted by hydrolysis and removal of ammonia to terephthalic acid. The ammonia that is generated by this hydrolysis is returned to the column through line 11 where it is eliminated with the overhead stream. Residence time in the reboiler is about 0.5 to 3 hours. It will be understood that although the reboiler 23 is shown separate from the distillation column 22, the reboiler may be an integral part of the bottom portion of the column as is frequently the case with industrial equipment. Finally, the slurry comprised of terephthalic acid in solution and in suspension is taken from the reboiler through line 6, cooled and the acid crystals of terephthalic acid (TPA) separated by filtration or other conventional means and the filtrate recycled through line 8 to the slurry tank 20.

When the TPN hydrolysis is carried out in the above described equipment in a conventional two phase hydrolysis operation at 250° C, plant stream flows for the TPA commercial plant (500 MM lbs/yr) are as shown in Table I.

TABLE I

| | Two Phase Operation Plant Stream Flows (Lb-Moles Per Hour) | | | | | | | | | | |
|---|---|---|---|---|---|---|---|---|---|---|---|
| | Stream Number (See FIG.) | | | | | | | | | | |
| Component | 1 | 2 | 3 | 4 | 5 | 6 | 7 | 8 | 9 | 10 | 11 |
| TPN | 382.7 | | 382.7 | | | | | | | | |
| ATA | | | 5.7 | 124.5 | | 5.7 | | 5.7 | | 124.5 | |
| DAT | | | 62.3 | 326.2 | | 62.3 | | 62.3 | | 326.2 | |
| TPH | | | | | | 14.1 | 14.1 | | | | |
| TPA | | | | | | 368.6 | 368.6 | | | | |
| NH$_3$ | | | | | 751.3 | | | | | | |
| H$_2$O | | 2890.7 | 20688.2 | 19276.2 | 751.3 | 18420.2 | 622.7 | 17797.5 | 4282.4 | 23558.6 | 5785.0 |
| Tot.Flow- | 48986 | 52033 | 434884 | 434884 | 26291 | 408589 | 74723 | 333866 | —* | 511968 | —* |

*Constant molal overflow operation of column is assumed. Actual compositions of Streams 9 and 11 depend on condenser performance and they vary along length of column.
Legend
TPN - Terephthalonitrile
ATA - Ammonium terephthalamate
DAT - Diammonium terephthalate
TPH - Terephthalamic acid
TPA - Terephthalic acid When the hydrolysis is carried out at 250° C as the three phase system of the invention, the plant stream flows for the same plant are given in Table II.

TABLE II

| | Three Phase Operation Plant Strean Flows (Lb-Moles Per Hour | | | | | | | | | | |
|---|---|---|---|---|---|---|---|---|---|---|---|
| Component | 1 | 2 | 3 | 4 | 5 | 6 | 7 | 8 | 9 | 10 | 11 |
| TPN | 382.7 | | 382.7 | | | | | | | | |
| ATA | | | 4.1 | 169.4 | | 4.1 | | 4.1 | | 169.4 | |
| DAT | | | 36.8 | 254.1 | | 36.8 | | 36.8 | | 254.1 | |
| TPH | | | | | | 12.7 | 12.7 | | | | |
| TPA | | | | | | 370.0 | 370.0 | | | | |
| NH$_3$ | | | | | 752.7 | | | | | | |
| H$_2$O | | 2893.5 | 8442.0 | 7076.6 | 752.7 | 6171.2 | 622.7 | 5548.5 | 4290.4 | 11367.0 | 5795.8 |
| Tot.Flow-lbs/hr | 48986 | 52084 | 209035 | 209035 | 26345 | 182691 | 74725 | 107966 | —* | 286262 | —* |

*Constant molal overflow operation of column is assumed. Actual compositions of Streams 9 and 11 depend on condenser performance and they vary along length of column.
Legend
TPN - Terephthalonitrile
ATA - Ammonium terephthalamate
DAT - Diammonium terephthalate
TPH - Terephthalamic acid
TPA - Terephthalic acid A comparison of the significant differences between the two and three operation systems is shown in Table III.

TABLE III

|  | Two-Phase Operation | Three-Phase Operation |
|---|---|---|
| Aromatics Concentration in Stripping Zone (Str. 10) (Molality) | 1.063 | 2.070 |
| Pure TPA Solubility (Molality) | 0.9036 | 0.9036 |
| Amide Nitrogen in Column Bottoms Product (Str. 6) - (ppm) | 3710 | 3340 |
| Amide Nitrogen in Final Products Acids (Str. 7) - (ppm) | 3110 | 2800 |
| Nitrogen Removal in Distillate Product - (% of Feed) | 83.3 | 88.9 |

It is quite clear from the above that the nitrogen removal by the process of the invention is significantly superior to the prior art two phase system and thus a terephthalic acid product of higher purity is obtained.

The invention claimed is:

1. A process for making terephthalic acid from terephthalonitrile in a distillation reactor system where enhanced ammonia removal is obtained which comprises the steps of:

(a) feeding an aqueous equilibrium hydrolysis solution of terephthalnoitrile to a reactive distillation column operated at a temperature between about 200° and about 260° C. at autogenous pressure, maintaining the molal concentration of aromatics in the aqueous liquid in said column sufficiently high to effect precipitation of dissolved terephthalic acid while subjecting the contents of said reactor to hydrolysis and distillation of ammonia, (b) removing ammonia and water vapor from the top of said column, (c) subjecting bottoms product in said column to further hydrolysis and distillation in a reboiler at a temperature of from about 200° to about 260° C. and returning vapors from the reboiler to the column, (d) removing an aqueous solution of product terephthalic acid containing suspended terephthalic acid solids from the reboiler, and (e) separating terephthalic acid product low in nitrogen impurities.

* * * * *